United States Patent [19]
Guegler et al.

[11] Patent Number: 6,083,727
[45] Date of Patent: Jul. 4, 2000

[54] METHODS AND COMPOSITIONS FOR PRODUCING 5' ENRICHED CDNA LIBRARIES

[75] Inventors: Karl Guegler, Menlo Park; Ruoying Tan, Foster City; Michael J. Rose, Palo Alto, all of Calif.

[73] Assignee: Incyte Pharmaceuticals Inc., Palo Alto, Calif.

[21] Appl. No.: 09/343,945

[22] Filed: Jun. 30, 1999

[51] Int. Cl.$^7$ .......................... C07H 21/02; C07H 21/04; C12P 19/34; C12Q 1/68
[52] U.S. Cl. ............................ 435/91.5; 435/91.1; 435/6; 536/23.1; 536/24.3
[58] Field of Search ............................... 435/6, 91.1, 91.2, 435/91.5; 536/23.1, 24.3, 24.33

[56] References Cited

PUBLICATIONS

Promega "Protocols & Applications Guide" 1991.
Pharmacia Biotech, 1996 Catalog p. 94–103.
Dear et al Mammalian Genome 7, 654–656 (1996).
Sambrook, Fritsch and Maniatis, Molecular Cloning: A Laboratory Manual, (Cold Spring Harbor Laboratory Press, 1989) Chapter 8, pp. 8.2–8.86.

*Primary Examiner*—George C. Elliott
*Assistant Examiner*—Karen A. Lacourciere
*Attorney, Agent, or Firm*—Bret Field; Bozicevic, Field & Francis LLP

[57] ABSTRACT

Methods are provided for preparing a double-stranded cDNA corresponding to the 5' end of an mRNA. In the subject methods, an mRNA is first contacted with an oligo dT primer under first strand cDNA synthesis conditions. Next, the resultant hybrid is contacted with a random primer under first strand cDNA synthesis conditions, such that a cDNA complementary to the 5' end of the mRNA is produced. The resultant hybrid molecule is converted to two different double-stranded cDNAs, a first cDNA comprising the oligo dT primer and a second cDNA lacking the oligo dT primer. The two double-stranded cDNAs are then separated from each other. The subject methods find use in a variety of applications, and find particular use in the synthesis of 5' enriched cDNA libraries. Also provided are cDNA libraries produced by the subject methods, as well as kits for performing the subject methods.

14 Claims, 1 Drawing Sheet

Construct 5' information-enriched cDNA libraries with double primed method

METHODS AND COMPOSITIONS FOR PRODUCING 5' ENRICHED CDNA LIBRARIES

TECHNICAL FIELD

The field of this invention is cDNA libraries.

BACKGROUND OF THE INVENTION

A complementary DNA or cDNA is a deoxyribonucleic acid that contains the information coding for the synthesis of proteins, but lacks the intervening introns present in genomic DNA. The synthesis and/or use of cDNA and/or libraries thereof plays a critical role in a variety of different applications in biotechnology and related fields. Applications in which cDNAs and/or libraries thereof are employed include gene discovery, differential gene expression analysis, and the like. A variety of protocols have been developed to prepare cDNA and libraries thereof, where such methods are continually being modified.

In standard methods currently used for the preparation of cDNA libraries, the mRNA in the cell is isolated by virtue of the presence of a polyadenylated tail present at its 3' end which binds to a resin specific for this structure (oligo dT-chromatography). The purified mRNA is then copied into cDNA using a reverse transcriptase, which starts at the 3' end of the mRNA and proceeds towards the 5' end. Second strand synthesis is then performed. Linkers are added to the ends of the double stranded cDNA to allow for its packaging into virus or cloning into plasmids. At this stage, the cDNA is in a form that can be propagated.

One disadvantage observed with current cDNA library synthesis protocols is that current methods tend to produce libraries having a significant proportion of incomplete cDNAs, which results from inefficiencies in the reverse transcriptase employed to generate the library. To compensate for the incomplete cDNA constituents of the library, investigators must perform many rounds of isolation (screenings) and construct a "full-length" cDNA from the accumulated pieces. Such processes are resource intensive and do not ensure that each initial mRNA is represented in the cDNA library.

In addition, there is significant under-representation of sequences close to the 5' end of mRNAs since in cDNA libraries produced by convention methods. This under-representation results from the fact that the reverse transcriptase will usually "fall off" before reaching these sequences. In many instances, the 5' information is of great interest.

Therefore, there is continued interest in the development of new methods of cDNA synthesis, particularly in methods capable of providing cDNAs containing 5' information.
Relevant Literature Sambrook, Fritsch & Maniatis, Molecular Cloning: A Laboratory Manual (Cold Spring Harbor Laboratory Press) (1989) chapter 8.

SUMMARY OF THE INVENTION

Methods are provided for preparing a double-stranded cDNA corresponding to the 5' end of an mRNA. In the subject methods, an mRNA is first contacted with an oligo dT primer under first strand cDNA synthesis conditions. Next, the resultant hybrid is contacted with a random primer under first strand cDNA synthesis conditions, such that a cDNA complementary to the 5' end of the mRNA is produced. The resultant hybrid molecule is converted to two different double stranded cDNAs, a first cDNA comprising the oligo dT primer and a second cDNA lacking the oligo dT primer. The two double stranded cDNAs are then separated from each other. The subject methods find use in a variety of applications, and find particular use in the synthesis of 5' enriched cDNA libraries. Also provided are cDNA libraries produced by the subject methods, as well as kits for performing the subject methods.

DEFINITIONS

Figure 1:
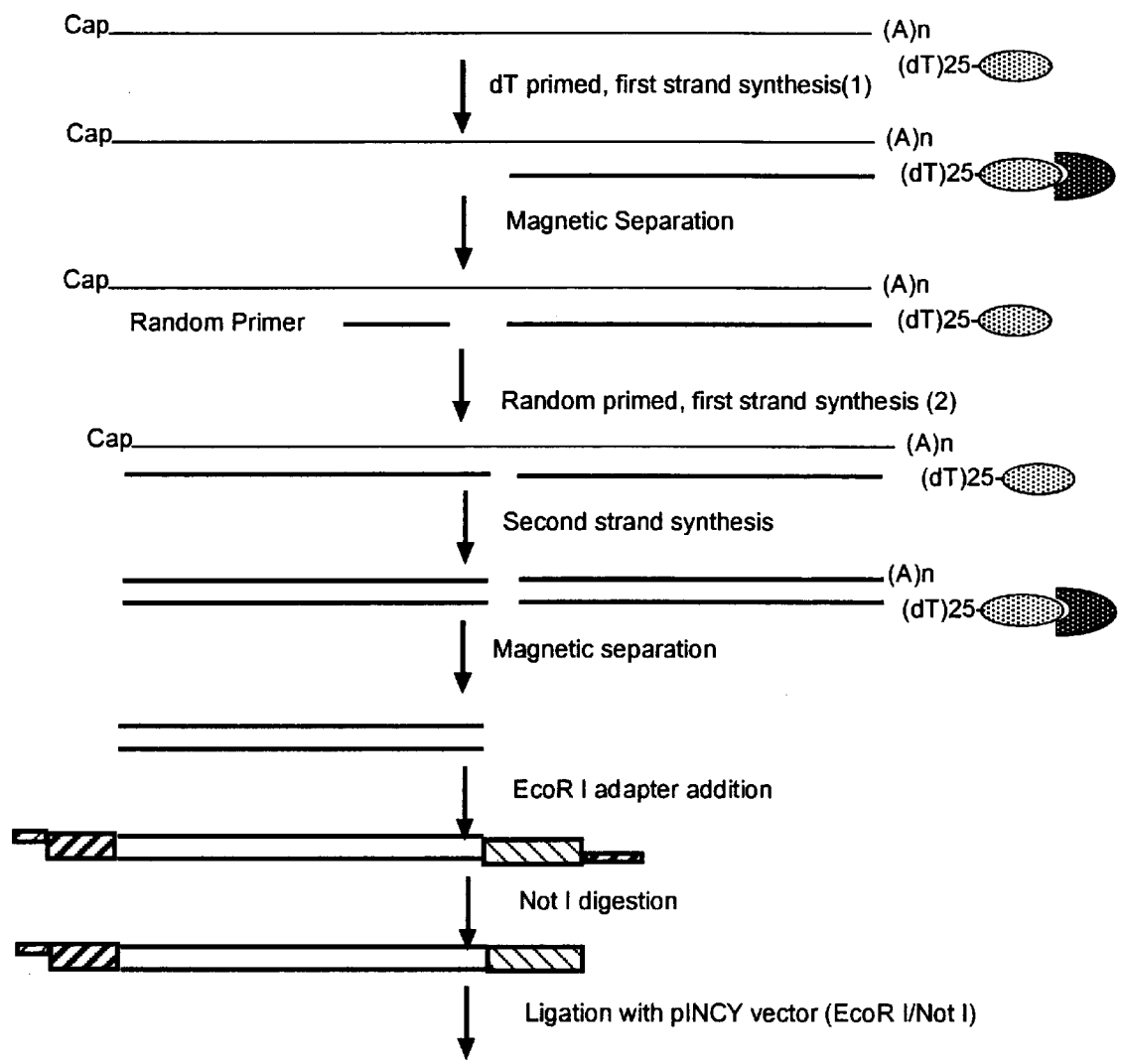
FIG. 1 provides schematic of the method according to the subject invention.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides in length.

The term "polynucleotide" as used herein refers to a single- or double-stranded polymer composed of nucleotide monomers of greater than about 120 nucleotides in length up to about 1000 nucleotides in length.

DESCRIPTION OF THE SPECIFIC EMBODIMENTS

Methods for preparing double stranded cDNAs from mRNAs, wherein the cDNAs comprise the 5' sequence information of the mRNAs, as well as kits for practicing the subject methods, are provided. The first step of the subject methods is to hybridize an oligo dT primer to the mRNA. Hybridization occurs under first strand cDNA synthesis conditions. As such, a hybrid molecule is produced. (In certain embodiments, the mRNA component of the hybrid molecule is longer than the cDNA component). The resultant hybrid molecule is then contacted with a random primer which results in additional first strand cDNA synthesis to a produce a second hybrid molecule. The second hybrid molecule is then converted to two double-stranded cDNA molecules, one of which corresponds to the 5' end of the mRNA and the second of which includes the oligo dT primer. The subject methods find particular use in the preparation of 5' enriched cDNA libraries.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

In the broadest sense, the subject invention is directed to methods of preparing double-stranded nucleic acid molecules from single-stranded nucleic acid molecules, and specifically to methods of preparing double-stranded deoxyribonucleic acid molecules from single-stranded ribonucleic acid molecules. Generally, the single-stranded ribonucleic acid molecule is an mRNA molecule having a polyA tail while the double-stranded deoxyribonucleic acid molecule is a cDNA molecule. In particular, the subject invention is directed to methods of producing double-stranded cDNA molecules that include the sequence information from the 5' end of the template mRNA from which they are prepared. The length of the cDNA molecules prepared by the subject methods typically ranges from about 0.5 to 3.0 kb, usually from about 1.0 to 2.0 kb and more usually from about 1.0 to 1.5 kb.

The first step in the subject methods is to prepare a first hybrid complex or duplex of a ribonucleic acid hybridized to a deoxyribonucleic acid compound. This first hybrid or duplex is prepared from the initial ribonucleic acid molecule, e.g. the mRNA. This step is generally accomplished by contacting the initial ribonucleic acid with a primer under conditions sufficient for template driven enzymatic deoxyribonucleic acid synthesis to occur. In most instances, this first step involves contacting an mRNA with a primer under first strand cDNA synthesis conditions, where the primer is generally an oligo dT primer.

The initial mRNA that serves as template in the first step may be present in a variety of different samples, where the sample will typically be derived from a physiological source. The physiological source may be derived from a variety of eukaryotic sources, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNAs to be analyzed from the physiological source from which it is derived, the physiological source may be subjected to a number of different processing steps, where such processing steps might include tissue homogenation, cell isolation and cytoplasmic extraction, nucleic acid extraction and the like, where such processing steps are known to those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989).

The oligo dT primer employed in the first step of the subject methods is sufficiently long to provide for efficient hybridization to the polyA tail. Generally, the length of the oligo dT primer ranges from about 10 to 35 nt in length, usually from about 10 to 30 nt in length, and more usually from about 20 to 25 nt length. In many embodiments, the oligo dT primer is stably attached to the surface of a solid support. The solid support may be any convenient solid support. A variety of different solid-phases are suitable for use in the subject methods, such phases being known in the art and commercially available. Specific solid phases of interest include polymeric supports, e.g. polystyrene, pegs, sheets, beads, magnetic beads, and the like. By stably attached is meant that the oligo dT primer remains associated with the surface of the solid support under at least conditions of enzymatic template driven nucleic acid synthesis. The oligo dT primer may be covalently or non-covalently bonded to the solid phase.

As stated above, the oligo dT primer is contacted with the mRNA under conditions sufficient for template driven enzymatic deoxyribonucleic acid synthesis to occur, where the mRNA molecule serves as the template molecule.

In addition to the mRNA and the primer, a reverse transcriptase and other reagents necessary for primer extension are present. A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), human T-cell leukemia virus type I (HTLV-I), bovine leukemia virus (BLV), Rous sarcoma virus (RSV), human immunodeficiency virus (HIV) and Thermus aquaticus (Taq) or Thermus thermophilus (Tth) as described in U.S. Pat. No. 5,322,770, the disclosure of which is herein incorporated by reference, avian reverse transcriptase, and the like. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like. Of particular interest because of their commercial availability and well characterized properties are avian reverse transcriptase and M-MLV. Additional reagents that may be present include: dNTPs; buffering agents, e.g. Tris-Cl; cationic sources, both monovalent and divalent, e.g. KCl, $MgCl_2$; suifhydril reagents, e.g. dithiothreitol; and the like.

The order in which the reagents are combined may be modified as desired. One protocol that may be used involves the combination of all reagents except for the reverse transcriptase on ice, then adding the reverse transcriptase and mixing at around 4° C. Following mixing, the temperature of the reaction mixture is raised to 37° C. followed by incubation for a period of time sufficient for first strand cDNA primer extension product to form, usually about 0.5 hour.

Contact of the initial ribonucleic acid, e.g. mRNA, with the primer, e.g. oligo dT primer, under conditions sufficient for first strand cDNA synthesis results in the production of a first hybrid or duplex which is made up of a ribonucleic acid hybridized to a deoxyribonucleic acid. The duplex is further characterized in that the cDNA molecule is hybridized to the 3' end of the mRNA molecule and therefore includes the 3' sequence information of the template mRNA molecule.

The second step of the subject methods is to contact the resultant hybrid or duplex prepared above, i.e. the first hybrid, with a random primer under conditions sufficient for template driven enzymatic deoxyribonucleic acid synthesis to occur. By random primer is meant a primer of random base sequence relative to the single-stranded RNA of the first hybrid, i.e. a primer that is not known with certainty to hybridize to the mRNA component of the first hybrid or duplex prior to use. In other words, the random primer has a sequence that is not known for certainty to have a complementary region in the single-stranded portion of the RNA of the hybrid prior to contact with the random primer. The random primer is sufficiently long to provide for efficient hybridization to a complementary region of the mRNA component of the first hybrid (if present), where the random primer typically ranges from about 4 to 40 nt, usually from about 10 to 30 nt and more usually from about 20 to 30 nt in length. Specific primers of interest include those that have from about 5 to 15, usually from about 6 to 9 nt random nts fused to a restriction enzyme cut sit of from about 5 to 20, usually from about 8 to 16 nt, e.g. 3'(N)$_9$GCGGCCGCGCGGCCGC5', where N is any nucleotide.

Contact of the random primer with the second hybrid may be accomplished using any convenient protocol. The second step of the subject invention may be accomplished by simply introducing the random primer into the reaction mixture containing the first hybrid. However, in most embodiments the first hybrid is first isolated prior to contact with the random primer by separating it from the remainder of the constituents of the reaction mixture from which it was produced. Separation may be by any convenient means. Where the oligo dT primer employed to produce the first hybrid is stably attached to a solid phase, a separation protocol based on the presence of the solid phase support may be employed. For example, where the solid phase is a magnetic solid phase, a magnetic based separation protocol may be employed, where such protocols are known to those of skill in the art. The isolated first hybrid is then contacted with the random primer in a new, second reaction mixture having conditions sufficient for template driven enzymatic deoxyribonucleic acid synthesis, where such conditions are described above.

Contact of the first hybrid or duplex with the random primer under conditions sufficient for template driven enzymatic deoxyribonucleic acid synthesis, e.g. first strand cDNA synthesis conditions (as described above), results in the production of a second hybrid or duplex which is made up of a single ribonucleic acid molecule having two separate deoxyribonucleic acid molecules hybridized to it. The first deoxyribonucleic acid molecule in the second hybrid includes the oligo dT primer employed in the first step of the method and is located at the 3' end of the ribonucleic acid. The second deoxyribonucleic acid molecule is hybridized to a region of the ribonucleic acid distal from the 3' terminus, and in many embodiments is hybridized to the 5' terminus of the ribonucleic acid. Of particular interest are second hybrids in which the second deoxyribonucleic acid molecule includes the genetic information of the 5' terminus of the ribonucleic acid, e.g. mRNA, to which the second deoxyribonucleic acid is hybridized. The length of the second deoxyribonucleic acid molecule typically ranges from about 500 to 3000 nt, usually from about 1000 to 2000 nt and more usually from about 1500 to 2000 nt.

The next step in the subject methods is to convert the second hybrid or duplex to double-stranded deoxyribonucleic acid molecules, specifically a first double-stranded cDNA molecule and a second double-stranded cDNA molecule. The first double-stranded cDNA produced by this conversion step lacks an oligo dT region, i.e. it does not include the oligo dT primer. The second double-stranded cDNA molecule differs from the first double-stranded cDNA molecule in that it does include an oligo dT region, i.e. it includes the original oligo dT primer. The two double-stranded cDNA molecules further differ from each other in that the second double-stranded cDNA molecule includes the sequence information from the 3' end of the original mRNA from which it is derived. In contrast, the first double-stranded cDNA molecule does not include the sequence information from the 3' end of the original mRNA, but instead includes sequence information from a non-3' region of the mRNA and preferably includes sequence information from the 5' end of the original mRNA.

The conversion of the second hybrid to double-stranded cDNAs may be accomplished using any convenient protocol, where suitable protocols are known to those of skill in the art. One technique which may be employed is the self-priming technique as described by Efstratiadis et al., Cell (1976)7: 279; Higuchi et al., Proc. Natl. Acad. Sci. (1976) 73: 3146; Maniatis et al., Cell (1976) 8: 163 and Rougeon and Mach, Proc. Natl. Acad. Sci. (1976) 73: 3418, in which the hybrid is denatured, e.g. by boiling or hydrolyzation of the mRNA with OH—, and the first strand cDNA is allowed to form a hairpin loop and self prime the second strand cDNA. Alternatively the method introduced by Okayama and Berg, Mol. Cell Biol. (1982) 2: 161 and modified by Gubler and Hoffman, Gene (1983) 25: 263 may be employed, in which the hybrid is used as a template for nick translation. Alternatively, one may use terminal transferase to introduce a second primer hybridization site at the 3' termini of the first strand, as described by Rougeon et al., Nucleic Acids Res. (1975) 2: 2365 and Land et al., Nucleic Acids Res. (1981) 9: 2251.

Following conversion of the second hybrid into first and second double-stranded deoxyribonucleic acids, e.g. cDNAs, the resultant first and second cDNAs are separated from each other. Any convenient separation protocol may be employed. In those embodiments in which the original oligo dT primer employed is stably associated with a solid support, a separation protocol that exploits the presence of this solid support, e.g. separation based on weight, size, etc., may be employed. In those preferred embodiments in which the support is magnetic, a magnetic separation protocol may be employed. Separation of the first and second double-stranded cDNAs results in isolated first double-stranded cDNA.

The resultant isolated first double-stranded cDNA may then be ligated into an appropriate vector for propagation and subsequent use, as desired, using methods well known to those of skill in the art. Appropriate vectors include viral, phagemid and plasmid vectors. Generally, this step involves contact of the vector with the double-stranded cDNA under conditions sufficient for ligation of the cDNA with the vector to occur. Typically, the vector and the cDNA will have been treated to produce complementary or "sticky-ends" with at least one, and preferably two different restriction endonucleases. This pretreatment step may further include ligation of linker or adapter sequences onto the ends of the vector and/or ds cDNA in order to introduce desired restriction sites, etc.

The subject invention finds particular use in the preparation of 5' enriched cDNA libraries. By 5' enriched is meant that a significant proportion of the cDNAs in the library contain the nucleotide sequence information of the 5' end of the mRNAs from which the cDNAs are derived. The 5' enriched cDNA libraries of the subject invention comprise at least 5, usually at least 50 and more usually at least 100 distinct cDNAs (i.e. cDNAs that differ in sequence from each other), where the number of distinct cDNAs in the library may be as high as 10,000 or higher. A significant portion of the cDNA constituents of the library include the 5' sequence information of their corresponding mRNA from which they were derived, where the percentage of distinct cDNAs in the library that include 5' sequence information from their corresponding mRNAs is at least about 10%, usually at least about 20% and more usually at least about 25%, where the percentage may be as high as 30% or higher, including in certain embodiments, 40%, 50%, 60% 70% 80%, 90% or higher.

Also provided by the subject invention are kits for carrying out the subject methods. The kits of the subject invention include at least an oligo dT primer and a random primer, where the oligo dT primer is, in many embodiments, stably attached to a solid support. The kit may further include one or more reagents for carrying out the claimed methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, T1 RNAse, and the like. A set of instructions will also typically be included, where the instructions may be associated with a package insert and/or the packaging of the kit or the components thereof.

The following examples are offered by way of illustration and not by way of limitation.

EXPERIMENTAL

A. First Strand Synthesis:

1. Wash Beads:

a. 1 mg $(dT)_{25}$-Biotin can bind 2 μg mRNA polyA$^+$, for 2.5 μg mRNA polyA$^+$ use 0.25 ml Dynabeads $(dT)_{25}$-Biotin (5 mg/ml) (5×0.25×2=2.5). Vortex the tube and suspend the beads well, take 0.25 ml of beads to a siliconized, Rnase-free tube.

b. Remove the supernatant by magnetic separation.

c. Wash the beads once with 100 μl binding buf.

2. First Strand Synthesis with Oligo-dT.

a. Annealing, add a mixture of 2.5 μl mRNA polyA$^+$ (1 μg/μl) and 7.5 μl ddw to the beads. Vortex, mix thoroughly.

b. 70° C., 10 min, chill on ice for 5 min, spin to collect and suspend.

c. First strand reaction with oligo-dT.

Add iced cocktail containing

| 4 μl   | 5 x 1st strand Buffer |
| 2 μl   | 0.1 M DTT             |
| 1 μl   | 10 mM dNTPs           |
| 1 μl   | ddw                   |

37° C. for 2 min to equilibrate the temperature, add 2 μl SuperScript II RT. Total 20 μl, mix, incubate at 37° C. for 0.5 hour (or try 1 hour), keep shaking with shake water bath.

d. Remove the supernatant by magnetic separation.

e. Wash the beads with 100 μl wash buffer, remove the supernatant by magnetic separation.

3. First Strand Synthesis with Random Primer a. Annealing, add 2.5 μl 0.25 μg/μl pN9 Not I primer and 6.5 μl ddw to the tube.

b. 37° C., 10 min (or try 70° C. 10 min), then put on ice.

c. First strand reaction with random primer

Add iced cocktail containing

| 4 μl   | 5 x 1st strand Buffer       |
| 2 μl   | 0.1 M DTT                   |
| 1 μl   | 10 mM dNTPs                 |
| 1 μl   | [α-$^{32}$P]dCTP (1 μCi/μl) |
| 1 μl   | ddw                         |

37° C. for 2 min to equilibrate the temperature, add 2 μl SuperScript II RT. Total 20 μl, mix, Incubate at 37° C. for 1 hour, with shaking.

d. Remove 2 μl to a new tube, for analysis.

B. Second Strand Synthesis a. On ice, add iced cocktail containing

93 μl ddw
30 μl 5×second strand buffer
3 μl 10 mM dNTP mix
1 μl *E. coli* DNA ligase (10 units/μl)
4 μl *E. coli* DNA polymerase I (10 units/μl)
1 μl *E. coli* Rnase H (2 units/μl)

Total 150 μl, incubate 16° C. for 2 hours, with shaking.

b. Add 2 μl T4 DNA polymerase (10 units), 16° C., 5 min.

c. Add 10 μl 500 mM EDTA.

d. By magnetic separation, transfer the supernatant to a new tube, total volume is 162 μl.

e. Add equal volume (162 μl) phenol, chloroform, isoamyl alcohol (25:24:1), vortex thoroughly and centrifuge at RT for 5 min, 14,000 g to separate the two phases, carefully remove the upper aqueous layer and transfer into a new tube.

f. Add ½ volume (81 μl) 7.5 M NH$_4$OAC, 5 μl 1 mg/ml yeast tRNA, 3 volume 100% ethanol (486 μl), mix, centrifuge at RT for 30 min at 14,000 g. Carefully remove the supernatant g. The pellet is washed with 200 μl of 70% ethanol (−20° C.), and spin for 2 min at 14,000 g, remove the supernatant and dry.

C. EcoR I Adapter Addition:

a. Pellet is suspended in 42.3 μl ddw,

| 5 μl   | 10 x NEB T4 DNA ligase buf |
| 1 μl   | 1 mg/ml EcoR I adaptors    |
| 1.7 μl | NEB T4 ligase              |

Total 50 μl, 16° C., 16 hours.

b. Add an equal volume of phenol:chloroform:isoamyl alcohol (25:24:1), vortex thoroughly, and centrifuge at room temperature for 5 min at 14,000 g to separate the two phases. Carefully remove the upper, aqueous layer and transfer it to a new centrifuge tube.

c. Add ½ volume 7.5 M NH$_4$OAC, 5 μl 1 mg/ml yeast tRNA, followed by 3 volumes 100% ethanol, Vortex the mixture thoroughly, and centrifuge at room temperature for 30 minutes at 14,000 g.

d. Carefully remove the supernatant and rinse the pellet gently wash with 200 μl 70% cold ethanol,. Centrifuge for 2 min at 14,000 g and remove the supernatant.

e. Lyophilize the pellet for 5 min to evaporate residual ethanol.

D. Not I Digestion:

a. To the adapted cDNA add the following reagents:

| 40.5 μl | ddw                                        |
| 5 μl    | 10 x NEB Not I Buf                         |
| 0.5 μl  | 100 x BSA                                  |
| 4 μl    | NEB Not I restriction enzyme (10 units/μl) |

Total volume of 50 μl, incubate @ 37° C. for 2~3 hrs.

b. Add an equal volume of phenol:chloroform:isoamyl alcohol (25:24:1), vortex thoroughly, and centrifuge at room temperature for 5 min at 14,000 g to separate the two phases. Carefully remove the upper, aqueous layer and transfer it to a new centrifuge tube.

c. Add ½ volume 7.5 M NH$_4$OAC, 5 μl 1 mg/ml yeast tRNA, followed by 3 volumes 100% ethanol, Vortex the mixture thoroughly, and centrifuge at room temperature for 30 minutes at 14,000 g.

d. Carefully remove the supernatant and rinse the pellet gently with 200 μl 70% cold ethanol, centrifuge for 2 min at 14,000 g and remove the supernatant.

e. Lyophilize the pellet for 5 min to evaporate residual ethanol.

E. Separate cDNA from Adapter by Size Fraction Column a. Place one of the cDNA size fractionation column in a support. Remove the top cat first, and then the bottom cap. Allow the excess liquid (20% ethanol) to drain.

b. Pipet 0.8 ml of TEN buffer [10 mM Tris-HCl (pH 7.5), 0.1 mM EDTA, 20 mM NaCl. Autoclaved] onto the upper frit and let it drain completely. Repeat this step three more times for a total 3.2 ml.

c. Label 20 sterile microcentrifuge tubes from 1 to 20, and place them in a rack with tube 1 under the outlet of the column.

d. Add 97 µl of TEN buffer to the cDNA pellets and mix gently.

e. Add the entire sample to the center of the top fritz and let it drain into the bed. Collect the effluent into tube 1.

f. Until it stops dripping, add 100 µl of TEN buffer to the column and collect the effluent into tube 2.

g. Beginning with the next 100 µl aliquot of TEN buffer, collect single-drop (~35 µl) fraction into individual tubes. Continue adding 100 µl aliquots of TEN buffer until you have collected a total 18 drops into tubes 3 through 20, one drop per tube.

h. Using an automatic pipet, measure the volume in each tube, use a fresh tip for each fraction to avoid cross-contamination. Record each value in column A. Identify the fraction for which the value in column is closest to, but not exceeding 500 µl.

i. Place the tubes in a scintillation counter and obtain Cerenkov counts for each fraction.

j. Based on cpm of each fraction, and total volume in column B (<550 µl), decide the fraction to be combined.

k. Add ½ volume 7.5 M NH$_4$OAC, 5 µl 1 mg/ml yeast tRNA, followed by 3 volumes 100% ethanol, Vortex the mixture thoroughly, and centrifuge at room temperature for 30 minutes at 14,000 g.

l. Carefully remove the supernatant and rinse the pellet gently with 200 µl 70% cold ethanol, Centrifuge for 2 min at 14,000 g and remove the supernatant.

m. Lyophilize the pellet for 5 min to evaporate residual ethanol.

n. Count the dry pellet to determine amount of cDNA yield.

F. Ligation and Transformation a. Re-suspend cDNA pellet to a concentration of 5 ng/µl.

b. For each sample prepare a tube with

| | |
|---|---|
| 31 µl | ddw |
| 4 µl | 5 ng/ul cDNA (20 ng) |
| 1 µl | pINCY vector (EcoR I-Not I) (50 mg) |
| 5 µl | 10 x NEB T4 DNA ligase buffer |
| 5 µl | T4 DNA ligase |

Total 50 µl, incubate at 16° C. for overnight.

c. Dilute 1 µl of ligation into 9 µl ddw.

d. Transform 1 µl of 1:10 dilution with 20 µl of DH-10B electrocompetent cells. Electroprate at 2.5KV.

e. Re-suspend transformed cells with 1 ml SOC (room temperature) and recovers in an incubator with shaking for one hour at 37° C.

f. Plate 10 and 100 µl of transformtion onto LB/2x carbencillin agar plates. Grow overnight at 37° C. and determine titer of ligation, titer per ng and titer per total amount of cDNA (titer/library).

G. Solutions and Reagents Needed

| Name | Company | Part No. |
|---|---|---|
| DYNABEADS mRNA Purification Kit | DYNAL | 610.01 |
| SUPERSCRIPT Plasmid System for cDNA Synthesis and Plasmid Cloning | GIBCOBRL | 18248-013 |
| EcoR I-Xho I adapter 5'-AATTCGGCTCGAG-3" 3'-GCCGAGCTC-5' | STRATAGENE | 901118 |
| α-$^{32}$P dCTP (3000 µci/Mmol, 10 mCi/Ml) | Amersham or ICN | |
| pNotI N9 3'-NNNNNNNNNGCGGCCGCGCGGCCGC-5' | | |
| Phenol:Chloroform:Isoamyl alcohol (25:24:1) | Amersham | US75831 |
| T4 DNA Ligase | NEB | 202s |
| Not I | NEB | 189s |
| mRNA (DNase treated) | Library group | |

It is evident from the above results and discussion that improved methods for preparing cDNA libraries are provided. With the subject methods, one can easily and efficiently prepare 5' enriched cDNA libraries. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of producing double-stranded deoxyribonucleic acid molecules from a single-stranded ribonucleic acid molecule comprising a polyadenylated tail, said method comprising:

(a) contacting said ribonucleic acid molecule with an oligo dT primer under conditions sufficient for template driven enzymatic deoxyribonucleic acid synthesis to occur, whereby a first hybrid molecule comprising said ribonucleic acid molecule hybridized to a first deoxyribonucleic acid molecule comprising said oligo dT primer is produced;

(b) isolating said first hybrid molecule;

(c) contacting said isolated first hybrid molecule with a random primer under conditions sufficient for template driven enzymatic deoxyribonucleic acid synthesis to occur, whereby said first hybrid molecule is converted to a second hybrid molecule comprising said first hybrid molecule and a second deoxyribonucleic acid molecule comprising said random primer and a sequence complementary to the 5' end of said ribonucleic acid molecule; and (d) converting said second hybrid molecule to a first double-stranded deoxyribonucleic acid molecule comprising said oligo dT primer and a second double-stranded deoxyribonucleic acid molecule comprising said random primer.

2. The method according to claim 1, wherein said method further comprises separating said first double-stranded deoxyribonucleic acid molecule from said second double-stranded deoxyribonucleic acid molecule.

3. The method according to claim 1, wherein said single-standed ribonucleic acid molecule is an mRNA.

4. The method according to claim 1, wherein said deoxyribonucleic acid molecules are cDNA.

5. The method according to claim 1, wherein said oligo dT primer is stably associated with the surface of a solid support.

6. A method of producing double-stranded cDNA molecules from a single-stranded mRNA molecule comprising a polyadenylated tail, said method comprising:

(a) contacting said mRNA molecule with an oligo dT primer under conditions sufficient for template driven enzymatic deoxyribonucleic acid synthesis to occur, whereby a first hybrid molecule comprising said mRNA molecule hybridized to a first cDNA molecule comprising said oligo dT primer is produced;

(b) isolating said first hybrid molecule;

(c) contacting said isolated first hybrid molecule with a random primer under conditions sufficient for template driven enzymatic deoxyribonucleic acid synthesis to occur, whereby said first hybrid molecule is converted to a second hybrid molecule comprising said first hybrid molecule and a second cDNA molecule comprising said random primer and a sequence complementary to the 5' end of said mRNA molecule;

(d) converting said second hybrid molecule to a first double-stranded cDNA molecule comprising said oligo dT primer and a second double-stranded cDNA molecule comprising said random primer; and (e) separating said first double-stranded cDNA molecule from said second double-stranded cDNA molecule.

7. The method according to claim 6, wherein said oligo dT primer is stably associated with a solid support.

8. The method according to claim 7, wherein said solid support is magnetic.

9. The method according to claim 8, wherein said separating is by magnetic separation.

10. The method according to claim 9, wherein said method further comprises introducing said second double-stranded cDNA molecule into a vector.

11. A method for producing a 5' enriched cDNA library from a sample of mRNA molecules comprising polyadenylated tails, said method comprising:

(a) contacting said mRNA molecules with an oligo dT primer under conditions sufficient for template driven enzymatic deoxyribonucleic acid synthesis to occur, whereby a population of first hybrid molecules comprising said mRNA molecules hybridized to a first population of cDNA molecules comprising said oligo dT primer is produced;

(b) isolating said population of first hybrid molecules;

(c) contacting said isolated population of first hybrid molecules with a random primer under conditions sufficient for template driven enzymatic deoxyribonucleic acid synthesis to occur, whereby said population of first hybrid molecules is converted to a population of second hybrid molecules, wherein each second hybrid molecule member of said population of second hybrid molecules comprises a first hybrid molecule and a second cDNA molecule comprising said random primer and a sequence complementary to the 5' end of said mRNA molecule;

(d) converting said population of second hybrid molecules to a first population of double stranded cDNA molecules comprising said oligo dT primer and a second population of double stranded cDNA molecules comprising said random primer; and (e) separating said first population of double-stranded cDNA molecules from said second population of double-stranded cDNA molecules;

whereby said 5' enriched library is produced.

12. The method according to claim 11, wherein said oligo dT primer is stably associated with a solid support.

13. The method according to claim 12, wherein said solid support is a magnetic support and said separating is by magnetic separation.

14. The method according to claim 11, wherein said method further comprises introducing said second population of double-stranded cDNA molecules into vectors.

* * * * *